United States Patent

Fehr et al.

Patent Number: 6,025,323
Date of Patent: Feb. 15, 2000

[54] USE OF CYCLIC KETONES IN PERFUMERY

[75] Inventors: Charles Fehr, Versoix; Christian Margot, Gilly, both of Switzerland

[73] Assignee: Firmenich SA, Geneva, Switzerland

[21] Appl. No.: 09/068,539

[22] PCT Filed: Sep. 12, 1997

[86] PCT No.: PCT/IB97/01092

§ 371 Date: May 13, 1998

§ 102(e) Date: May 13, 1998

[87] PCT Pub. No.: WO98/13447

PCT Pub. Date: Apr. 2, 1998

[30] Foreign Application Priority Data

Sep. 27, 1996 [CH] Switzerland ............... 2374/96

[51] Int. Cl.$^7$ ............... A61K 7/46; C07C 49/00; C07C 45/00; C07C 49/105; C07C 35/08
[52] U.S. Cl. ............... 512/22; 512/24; 512/25; 512/26; 512/27; 568/303; 568/338; 568/376; 568/700; 568/822; 568/832
[58] Field of Search ............... 512/22, 24, 25, 512/26, 27; 568/303, 338, 376, 700, 822, 832

[56] References Cited

U.S. PATENT DOCUMENTS

| | | | |
|---|---|---|---|
| 3,487,102 | 12/1969 | Blumenthal | 260/497 |
| 3,847,975 | 11/1974 | Hall | 252/522 |
| 3,962,148 | 6/1976 | Hochstetler et al. | 252/522 |
| 4,147,672 | 4/1979 | Schulte-Elte et al. | 252/522 |

FOREIGN PATENT DOCUMENTS

| | | |
|---|---|---|
| 0 210 391 | 2/1987 | European Pat. Off. . |
| 1 543 320 | 10/1968 | France . |
| 31 12 056 | 10/1982 | Germany . |
| 623 802 | 6/1981 | Switzerland . |

OTHER PUBLICATIONS

Hart, Harold, "Organic Chemistry", See 15.10 pp. 418–419, 1991.
Arctander et al., "Perfume and flavor chemical", see 967:dihydro–iso–phorone (1969).
Garnero et al., "New constituents of essential oil of iris rhizomes", *Chemical Abstracts* 95:327.
Guiard et al., "Réactivité des Diméthyl–4,4 cyclohexanones substituées en 2", *Bulletin de la Société Chimique de France*, No. 12, pp. 3021–3030 (1974).
Smith et al., "The Reduction–Methylation of Cyclohexenone Derivatives", *J. Org. Chem.* 32:2851–2856 (1967).
Derwent WPI Acc No. 87–030675/198705, English language abstracts for EP 210 391 (1987).
Derwent WPI Acc No. 82–86106E/198241, English language abstracts for Germany 31 12 056 (1982).

*Primary Examiner*—Cynthia Harris
*Assistant Examiner*—Monique Cole
*Attorney, Agent, or Firm*—Pennie & Edmonds LLP

[57] ABSTRACT

The compounds of formula

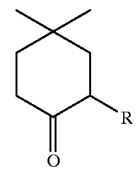

(I)

in which R stands for a methyl or ethyl group, are used as perfume ingredients for the preparation of perfuming compositions and perfumed articles, to which they confer aromatic and thujonic notes. The compounds can be used in the form of a mixture of enantiomers or in an enantiomerically pure state. The invention also comprises original processes for the preparation of these compounds.

12 Claims, No Drawings

USE OF CYCLIC KETONES IN PERFUMERY

TECHNICAL FIELD

The present invention relates to the field of perfumery. It concerns, more particularly, the use of a compound according to the formula

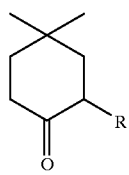

(I)

in which R stands for a methyl or ethyl radical, as a perfuming ingredient.

PRIOR ART

In spite of the fact that the chemical structure of the compounds according to formula (I) has been known for a long time (see, for example, B. Guiard et al, Bull. Soc. Chim. Fr. 1974, 3021), we were not able to find in the literature any description of potential odor properties of the named compounds. In fact, to our knowledge, no document of the prior art suggests the use of the compounds according to the present invention as perfuming ingredients for the preparation of perfuming bases or perfumes, as well as perfumed consumer products.

DESCRIPTION OF THE INVENTION

Now, we have discovered that the ketones of formula (I) are very useful perfuming ingredients, in particular for the preparation of perfuming compositions or a variety of perfumed products, to which they impart an odor of the aromatic and thujonic type.

Amongst the compounds of formula (I), 2-ethyl-4,4-dimethyl-1-cyclohexanone is cited as a preferred compound. This compound possesses an asymmetric carbon atom (in position 2 in the cycle) and may present itself as a racemic mixture of enantiomers when prepared in a conventional organic synthesis, or in the form of one of the enantiomers. We were able not only to prepare said mixture, but also the two enantiomers in a pure state and found differences in their odor notes.

The racemic mixture develops an odor of the thujonic type which is reminiscent of the typical odor of cedarleaf and of hyssop, accompanied by a natural fruity, damascenone character which is very much appreciated. The hyssop type character is quite natural as well.

The odor of this compound is moreover reminiscent of that of 3,3-dimethyl-cyclohexyl-methyl-ketone (see FR 1.543.320), but its aromatic-thujonic note is distinctly less camphoraceous and possesses a fruity aspect which is more pronounced than in the latter one. Furthermore, even if the odor of 2-ethyl-4,4-dimethyl-1-cyclohexanone is reminiscent of the odor of 5-methyl-exo-tricyclo[6.2.1.0(2,7)]undecan-4-one (see U.S. Pat. No. 5,538,944), this compound of formula (I) develops a fragrance which is distinctly more natural in its thujonic connotation.

As regards the two pure enantiomers of this compound (−)-(2R)-2-ethyl-4,4-dimethyl-1-cyclohexanone develops the more strongly herbaceous and thujonic odor of the two, with a pronounced fruity subnote having almost a spicy-berry-like character.

(+)-(2S)-2-Ethyl-4,4-dimethyl-1-cyclohexanone also possesses a herbaceous odor note, which however is less thujonic and drier than that of its enantiomer. Additionally, an earthy, rooty cellar aspect is also present.

By preparing mixtures which contain the enantiomers in different amounts, a person skilled in the art will be able to create fragrances according to the invention in which the characteristics of the enantiomers are combined at their best. In fact, hereinafter, whenever we refer to 2-ethyl-4,4-dimethyl-1-cyclohexanone this is meant to designate either one of its pure enantiomers or any mixture thereof.

The methylated homologue, namely 2,4,4-trimethyl-1-cyclohexanone, possesses a nice aromatic note which is appreciated for its fruity-eucalyptus connotation.

From the foregoing, it is evident that the compounds of formula (I) bring a new range of fragrant tones to the perfumer's palette.

Due to their fragrant properties, the compounds of formula (I), in the form of a mixture of enantiomers or as one of the pure enantiomers, find applications in fine fragrances as well as in technical perfumery. They may be used as such or in admixture with other perfuming ingredients, solvents or adjuvants of current use in the art.

The proportions in which these compounds can be used depend of the desired olfactory effect, as well as on the nature of the other perfuming coingredients. As an example, one can cite concentrations in the order of 0.1 to 10%, or even 20% or more by weight, with respect to the weight of the perfuming composition or the perfume into which they are incorporated.

When used for perfuming functional articles, like soaps, bath or shower gels shampoos or other hair-care-products, cosmetic preparations, body deodorants or air fresheners, detergents or fabric softeners, or household products, lower concentrations are generally employed. The values of these concentrations depend on the nature of the article or final perfumed product as well as on the desired olfactory effect, and a person skilled in the art will be capable of choosing these as a function of these parameters. Articles, such as perfuming or deodorizing products may thus typically contain from 0.1 to 1% by weight of a perfuming composition prepared according to the present invention.

The ketones of formula (I) are known compounds which can be prepared using standard reaction conditions (see, for example, B. Guiard et al., Bull Soc. Chim. Fr. 1974, 3028–3029, or U.S. Pat. No. 4,147,672, or H. A. Smith et al., J. Org. Chem. 1967, 32, 2851).

According to the invention, these compounds can be obtained, as a racemic mixture, following an original process under the particular conditions which will be laid out hereinafter.

The process of the invention which is used for the preparation of the compounds of formula

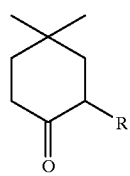

(I)

as a racemic mixture, is actually characterized in that a compound of formula

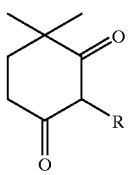

(II)

in which R stands for a methyl or ethyl radical, is hydrogenated in the presence of palladium on charcoal in an appropriate solvent to form the desired compound.

By appropriate solvent is meant here a polar solvent which is capable of dissolving the starting ketone of formula (II). As appropriate solvents, one can cite, for example, ethanol or isopropanol.

According to a preferred embodiment of the above-mentioned process, the reaction is carried out at room temperature in ethanol.

The starting products of formula (II) can be prepared as is described in the patent application DE 3,112,056.

The enantiomers of compounds (I) can be obtained by a multistep process described in the scheme below:

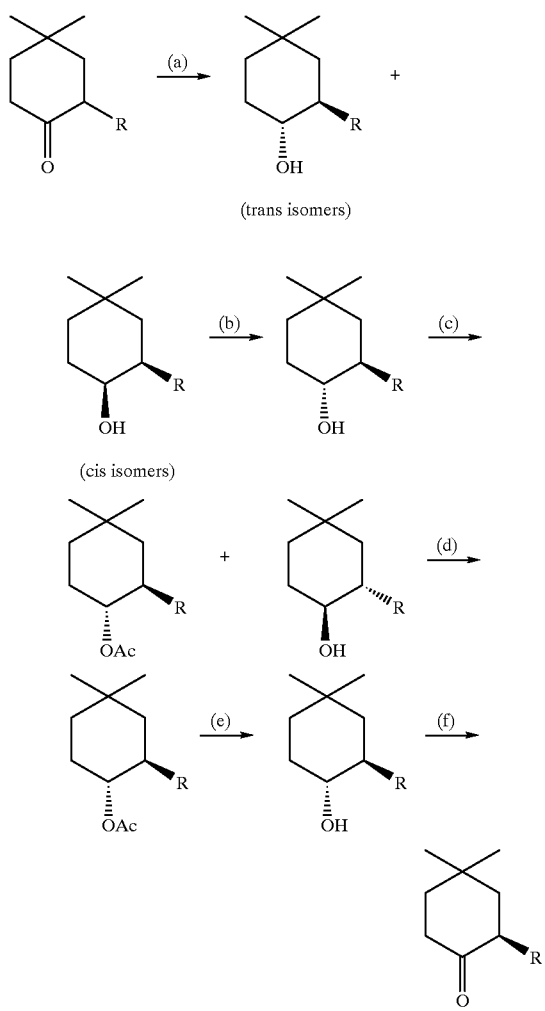

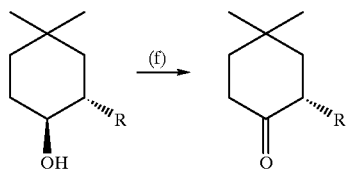

R = CH$_3$, C$_2$H$_5$ a) Na/appropriate alcohol
b) chromatographic separation of compounds
c) Novozym® 435/vinylacetate
d) chromatographic separation of compounds
e) saponification/reduction of ester
f) oxidation of alcohol to ketone The particular conditions of the above-cited reactions are described in detail in the examples below.

The present invention will now be described in greater detail using the following examples. In the preparation examples, the temperatures are indicated in degrees centigrade and the abbreviations have the usual meaning in the art.

EMBODIMENTS OF THE INVENTION

EXAMPLE 1

Preparation of 2-ethyl-4,4-dimethyl-1-cyclohexanone and of 2,4,4-trimethyl-1-cyclohexanone Under a nitrogen atmosphere, 1.0 g (0.6 mmol) of 2-ethyl-4,4-dimethyl-cyclohexane-1,3-dione (partially enolized; prepared as described in DE 3,112,056) is hydrogenated at ambient pressure and room temperature in ethanol (20 ml) in the presence of palladium on charcoal (5%, 100 mg). After 8 h, the mixture is filtered over Celite® and concentrated, and 0.8 g of a colorless oil are isolated and distilled in a bulb-to-bulb apparatus at a temperature of 70° C. and a pressure of $4 \times 10^2$ Pa.

690 mg (yield: 69%) of 2-ethyl-4,4-dimethyl-1-cyclohexanone containing 8% of 2-ethyl-6,6-dimethyl-1-cyclohexanone are isolated. By slow redistillation in a bulb-to-bulb apparatus and discarding a low-boiling fraction, the desired compound was isolated in a pure state (GC: 96%).

MS: 154(M$^+$, 52), 139(20), 126(100), 111(32), 97(58), 83(38), 70(52), 57(42), 55(56), 41(29)

NMR($^1$H, 360 MHz, CDCl$_3$): 0.87(t, J=7.5, 3H); 1.01(s, 3H); 1.15(m, 1H); 1.21(s, 3H); 1.31(t, J=13, 1H); 1.62(m, 1H); 1.70(m, 1H); 1.73–1.84(m, 2H); 2.22(m, 1H); 2.30(m, 1H); 2.45(m, 1H) δ ppm NMR($^{13}$C): 213.8(s); 47.6(d); 46.3(t); 40.1(t); 38.5(t); 31.5(q); 30.8(s); 24.6(q); 22.0(t); 11.7(q) δ ppm When working like indicated above, but replacing 2-ethyl-4,4-dimethyl-cyclohexane-1,3-dione by the appropriate compound of formula (II), namely 2,4,4-trimethyl-cyclohexane-1,3-dione (prepared as described in DE 3,112, 056), 2,4,4-trimethyl-1-cyclohexanone was obtained and showed the following analytical data:

NMR($^1$H, 360 MHz, CDCl$_3$): 0.99(d, J=7.0, 3H); 1.01(s, 3H); 1.22(s, 3H); 1.36(t, J=13.5, 1H); 1.65(dq, J=5.4, 13.5, 1H); 1.7(m, 2H); 2.25(ddd, J=3.5, 4.5, 14, 1H); 2.5(m, 211) δ ppm

MS: 140(M$^+$, 50), 125(20), 97(40), 85(100)

EXAMPLE 2

Preparation of (−)-(2R)-2-ethyl-4,4-dimethyl-1-cyclohexanone and of (+)-(2S)-2-ethyl-4,4-dimethyl-1-cyclohexanone Steps (a), (b): Reduction of 2-ethyl-4,4-dimethyl-1-cyclohexanone Within 6 h, sodium pieces of about 2 g weight (totally 36 g, 1.56 mol) were added, at 25° and under nitrogen, to a stirred solution of 2-ethyl-4,4-dimethyl-1-cyclohexanone (18.0 g, 117 mmol) in n-propanol (800 ml). The solution was stirred for 62 hours, cooled to 0°, hydrolyzed with HCl conc. (about 150 ml) and the product was extracted with ether (2×). The ether solution was washed, dried over $Na_2SO_4$, concentrated and the resulting mixture of trans-2-ethyl-4,4-dimethyl-cyclohexanol and cis-2-ethyl-4,4-dimethyl-cyclohexanol was chromatographed over $SiO_2$ using a 98:2 mixture of cyclohexane/ethylacetate, to provide, successively, a mixture constituted of 80% trans- and 20% cis-2-ethyl-4,4-dimethyl-1-cyclohexanol (11.0 g, 60%), and then just the pure trans isomer of this alcohol. The latter presented the following analytical data (7.19 g, 39%).

MS: 156($M^+$,2), 138(16), 123(58), 109(21), 97(43), 81(41), 69(32), 67(26), 57(100), 55(52), 41(54), 29(30)

NMR ($^1$H, 360 MHz, $CDCl_3$): 0.85(m, 1H); 0.89(t, J=7.5, 3H); 0.92(s, 3H); 0.94(s, 3H), 1.05–1.50(m, 6H); 1.53(br. 1H disappears with $D_2O$); 1.88(m, 2H); 3.17(ddd, J=11, 11 and 4.5, 1H) $\delta$ ppm NMR($^{13}$C): 75.0(d); 43.1(t); 41.9(d); 37.8(t); 32.7(q); 31.8(t), 30.4(s), 24.8(q+t), 10.7(q) $\delta$ ppm Steps (c), (d): Enantioselective Esterification of Trans-2-ethyl-4,4-dimethyl-1-cyclohexanol A mixture of the above-mentioned cyclohexanol (7.0 g, 45.0 mmol), Novozym® 435 (*Candida antarctica B*, available from Novo Nordisk A/S, Bagsvaerd, Denmark) (0.9 g) and vinyl acetate (6.25 g, 73 mmol) was stirred over 24 h at 25°. The mixture was filtered, concentrated and chromatographed over $SiO_2$ using cyclohexane/ethylacetate as eluant. The (−)-(1R,2R)-2-ethyl-4,4-dimethyl-1-cyclohexylacetate (4.0 g, 45%) was first isolated, followed by (+)-(1S,2S)-2-ethyl-4,4-dimethyl-1-cyclohexanol (2.49 g, 35%). The two products were finally distilled in a bulb-to bulb apparatus (oven 75°, 1.33×10² Pa)

(−)-(1R,2R)-2-ethyl-4,4-dimethyl-1-cyclohexylacetate
$[\alpha]^{25}_D$ ($CHCl_3$,c=0.04)=−75.8°

MS: 138(23), 123(40), 109(41), 95(15), 82(16), 67(26), 55(30), 43(100), 41(41)

NMR ($^1$H, 360 MHz,$CDCl_3$): 0.84(t, J=7.5, 3H); ~0.9(m, 1H); 0.92(s, 3H); 0.94(s, 3H); 1.03(m, 1H); 1.23–1.62(m, 6H); 1.81(m, 1H); 2.05(s, 3H); 4.43(ddd, J=11, 11 and 4.5, 1H) $\delta$ ppm NMR($^{13}$C) : 170.9(s); 77.6(d); 43.1(t); 38.9(d); 37.3(t); 32.6(g); 30.3(s); 27.9(t); 24.8(t); 24.7(q); 21.3(q); 10.7(q) $\delta$ ppm (+)-(1S,2S)-2-ethyl-4,4-dimethyl-1-cyclohexanol
$[\alpha]^{25}_D$ ($CHCl_3$,c=0.05)=+66.50°

Step (e): Reduction of (−)-(1R,2R)-2-ethyl-4,4-dimethyl-1-cyclohexylacetate

The above compound (3.0 g, 15.2 mmol) was added dropwise to a suspension of $LiAlH_4$ (360 mg, 9.47 mmol) in ether (30 ml) under reflux. After complete addition, the mixture was heated to reflux for 30 min and then hydrolyzed with NaOH 5% (4 ml). The white pasty precipitate was filtered, dried ($Na_2SO_4$), concentrated and a white oil was distilled in a bulb-to-bulb apparatus (oven 80°, 3 Torr). 2.3 g (96%) of (−)-(1R,2R)-2-ethyl-4,4-dimethyl-1-cyclohexanol were isolated. The compound showed an enantiomeric excess of 98%, determined by chiral GC (Megadex : 90° (6 min); 2.5°/min until 180°; p=16.7).

Step (f): Oxidation of (+)-(1S,2S)-2-ethyl-4,4-dimethyl-1-cyclohexanol and of (−)-(1R,2R)-2-ethyl-4,4-dimethyl-1-cyclohexanol Oxidation of (+)-(1S,2S)-2-ethyl-4,4-dimethyl-1-cyclohexanol 2.8 ml of Jones' reagent (2.5 M, 7.0 mmol), prepared according to Fieser, vol. 1, p. 142 ($CrO_3+H_2SO_4+H_2O$) were added dropwise to a stirred solution of (+)-(1S,2S)-2-ethyl-4,4-dimethyl-1-cyclohexanol (1.09 g, 7.0 mmol) in acetone (70 ml) at 5°. The temperature rose to 7°, and a green suspension was formed. Stirring was continued for 10 min, the reaction mixture was then poured on a mixture of ice/NaCl/pentane, extracted with pentane, washed, dried, concentrated, and the crude product (1.40 g) was distilled in a bulb-to-bulb apparatus (oven 70°, 3 Torr). 1.01 g of (+)-(2S)-2-ethyl-4,4-dimethyl-1-cyclohexanone were obtained (yield 91%).

The enantiomeric excess of 99% was determined by chiral GC (Megadex: 90° (6 min); 2.5°/min until 180°; P=16.7).

Oxidation of (−)-(1R,2R)-2-ethyl-4,4-dimethyl-1-cyclohexanol

By proceeding as described above for the oxidation of its enantiomer, the above cyclohexanol (1.56 g, 10.0 mmol) was oxidized to (−)-(2R)-2-ethyl-4,4-dimethyl-1-cyclohexanone (1.36 g, 88%, 97% e.e. determined under the conditions described above).

$[\alpha]^{25}_D$ ($CHCl_3$,c=0.07)=−29.3°.

EXAMPLE 3

Preparation of a Perfuming Composition

A base perfuming composition of the cologne type was prepared by admixing the following ingredients:

| Ingredient | Parts by weight |
|---|---|
| Linalyl acetate | 320 |
| Anisic aldehyde redist. | 70 |
| 50% * Habanolide ®[1] | 30 |
| Lavandin essential oil | 60 |
| 10% * Crystalmoss | 150 |
| Amyl salicylate | 320 |
| Total | 950 |

* in dipropyleneglycol (DIPG)
[1] cyclopentadecenolide; origin: Firmenich SA, Geneva, Switzerland By adding 50 parts by weight of 2-ethyl-4,4-dimethyl-1-cyclohexanone to this base composition of the herbaceous type, a thujonic, enriching aspect is conferred to this composition and there is imparted to it the connotation of a masculine cologne. On the other hand, when adding to this base composition 50 parts by weight of 2,4,4-trimethyl-1-cyclohexanone, a new composition is obtained, the odor of which possesses a fresher aspect.

EXAMPLE 4

Preparation of a Perfuming Composition

A base perfuming composition of the masculine cologne type having a green, citrus type odor was prepared by admixing the following ingredients:

| Ingredient | Parts by weight |
|---|---|
| Terpenyl acetate | 100 |
| 10% * Undecylenic aldehyde | 20 |
| Allyl amyl glycolate | 20 |
| 4-Cyclohexyl-2-methyl-2-butanol[1] | 60 |

| Ingredient | Parts by weight |
| --- | --- |
| 10% * α-Damascone[2)] | 15 |
| Dihydromyrcenol ®[3)] | 300 |
| Galbex ®[4)] 183 | 30 |
| 10% * Geranyl nitrile | 70 |
| 50% * Habanolide ®[5)] | 50 |
| Iralia ®[6)] | 30 |
| Lorysia ®[7)] | 125 |
| Crystalmoss | 10 |
| Polysantol ®[8)] | 10 |
| Benzyl salicylate | 155 |
| Total | 990 |

* in dipropyleneglycol
[1)]origin: Firmenich SA, Geneva, Switzerland
[2)]origin: Firmenich SA, Geneva, Switzerland
[3)]2,6-dimethyl-7-octen-2-ol; origin: International Flavors & Fragrances, USA
[4)]origin: Firmenich SA, Geneva, Switzerland
[5)]see Example 2
[6)]methyl-ionone; origin: Firmenich SA, Geneva, Switzerland
[7)]4-(1,1-dimethyl)-1-cyclohexyl acetate; origin: Firmenich SA, Geneva, Switzerland
[8)]3,3-dimethyl-5-(2,2,3-trimethyl-3-cyclopenten-1-yl)-4-penten-2-ol; origin: Firmenich SA, Geneva, Switzerland The addition of only 10 parts by weight of 2-ethyl-4,4-dimethyl-1-cyclohexanone to this cologne of the citrus-green type confers a much appreciated aromatic note to it, which note was totally absent beforehand. This base cologne thus acquired a more sophisticated and richer tonality, more modern and more natural and this in spite of the very small amount of product added.

On the other hand, the addition of 10 parts by weight of 2,4,4-trimethyl-1-cyclohexanone to this masculine base cologne imparted a nice aromatic-fruity aspect to the composition, which nevertheless included a more camphoraceous-earthy connotation than that obtained with the above-mentioned 2-ethyl-4,4-dimethyl-1-cyclohexanone.

What is claimed is:

1. A method to confer, enhance, improve or modify the odor properties of a perfuming composition or a perfumed article, which method comprises adding to said composition or article a compound of formula

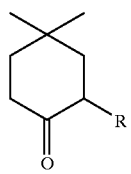

(I)

in which R stands for a methyl or ethyl group, in the form of a mixture of enantiomers or in the form of one of said enantiomers.

2. The method according to claim 1 wherein the compound is of formula

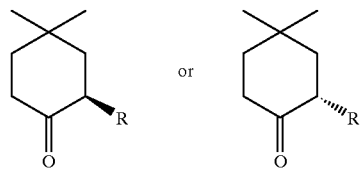

in which R stands for a methyl or ethyl group.

3. The method according to claim 1 wherein the compound is of formula

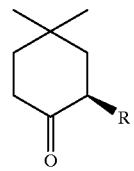

in which R stands for a methyl or ethyl group and the compound possess a herbaceous and thujonic odor with fruity subnote having a spicy-berry-like character.

4. The method according to claim 1 wherein the compound is of the formula

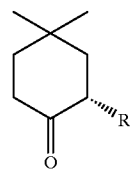

in which R stands for a methyl or ethyl group and the compound possess a herbaceous and thujonic odor with an earthy rooty cellar character.

5. The method according to claim 1 wherein the compound of formula I is present in an amount of between 0.1% to about 20% of the perfuming composition.

6. The method according to claim 3 wherein the compound is present in an amount of between 0.1% to about 20%.

7. The method according to claim 4 wherein the compound is present in an amount of between about 0.1% to about 20%.

8. Perfuming composition or perfumed article containing as active perfuming ingredient a compound of formula

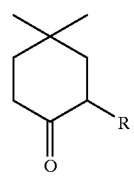

(I)

in which R stands for methyl or ethyl group, the latter being present in the form of a mixture of enantiomers or in the form of one of said enantiomers.

9. Perfumed article according to claim 8, in the form of a perfume or a cologne, a soap, a bath or shower gel, a shampoo or another hair care product, a body deodorant or an air freshener, a detergent or a fabric softener, or a household cleaner.

10. Process for the preparation of a compound of formula

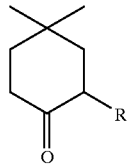
(I)

in which R stands for a methyl or ethyl group, characterized in that a cyclic diketone of formula

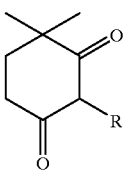
(II)

wherein R is defined as above, is hydrogenated in the presence of palladium on charcoal in an appropriate solvent.

11. Process for the preparation of a compound of formula

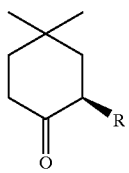 or 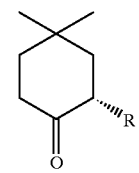

wherein R represents a methyl or ethyl group, which process is characterized in that an alcohol of formula

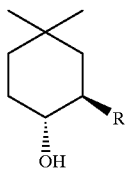, respectively 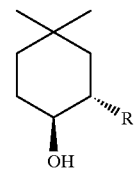

wherein R is defined as above, is oxidized by means of an appropriate oxidizing agent.

12. An optically active compound of formula

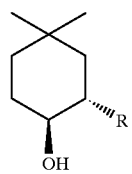

wherein R represents a methyl or ethyl group.

* * * * *